(12) United States Patent
Powers et al.

(10) Patent No.: US 12,345,138 B2
(45) Date of Patent: Jul. 1, 2025

(54) WELL PERFORATOR EVALUATION SYSTEM AND METHOD

(71) Applicant: GEODYNAMICS, INC., Millsap, TX (US)

(72) Inventors: Seth Powers, Weatherford, TX (US); Michael D. Wroblicky, Weatherford, TX (US); Chris Pool, Weatherford, TX (US); Jarrod Henry Pearson, Weatherford, TX (US); John T. Hardesty, Ft. Worth, TX (US)

(73) Assignee: GEODYNAMICS, INC., Millsap, TX (US)

( * ) Notice: Subject to any disclaimer, the term of this patent is extended or adjusted under 35 U.S.C. 154(b) by 591 days.

(21) Appl. No.: 17/389,482

(22) Filed: Jul. 30, 2021

(65) Prior Publication Data

US 2022/0034204 A1    Feb. 3, 2022

Related U.S. Application Data

(60) Provisional application No. 63/059,510, filed on Jul. 31, 2020.

(51) Int. Cl.
*E21B 43/116* (2006.01)
*E21B 43/117* (2006.01)
*F42B 35/00* (2006.01)
*G01N 33/22* (2006.01)

(52) U.S. Cl.
CPC ......... *E21B 43/116* (2013.01); *E21B 43/117* (2013.01); *F42B 35/00* (2013.01); *G01N 33/227* (2013.01)

(58) Field of Classification Search
CPC ............................ E21B 43/116; E21B 43/117
See application file for complete search history.

(56) References Cited

U.S. PATENT DOCUMENTS

| 3,894,489 A * | 7/1975 | Riedl ...................... F42B 12/18 |
| | | 102/308 |
| 6,223,656 B1 * | 5/2001 | Glenn ...................... F42B 3/08 |
| | | 102/306 |
| 8,549,905 B2 * | 10/2013 | Brooks ................... E21B 43/11 |
| | | 175/50 |
| 2020/0270973 A1 * | 8/2020 | Baumann .............. E21B 43/117 |

FOREIGN PATENT DOCUMENTS

| CN | 1392327 A | * | 1/2003 |
| CN | 1900481 A | * | 1/2007 |
| SU | 1190008 A1 | * | 11/1985 |

\* cited by examiner

*Primary Examiner* — Jill E Culler
(74) *Attorney, Agent, or Firm* — Morgan, Lewis & Bockius LLP

(57) ABSTRACT

A testing system for a shaped charge of a perforating gun, the testing system including a housing; a casing assembly located inside the housing; a perforating gun having at least one shaped charge, the perforating gun being located within the casing assembly; a sample material located within the housing, and in direct contact with the casing assembly; a wellbore accumulator in direct contact with the casing assembly and configured to supply a first fluid, at a wellbore pressure, inside the casing assembly; and a formation accumulator in direct contact with the sample material and configured to supply a second fluid, at a formation pressure, on the sample material.

9 Claims, 7 Drawing Sheets

WELL PERFORATOR EVALUATION SYSTEM AND METHOD

BACKGROUND

Technical Field

Embodiments of the subject matter disclosed herein generally relate to evaluating the performance of shaped charges, which are carried by a perforating gun, for making perforations into a casing of a well, and more specifically, to a system for testing the shaped charges with actual rock samples under conditions as close as possible to the conditions in a well.

Discussion of the Background

In the oil and gas field, to extract the oil from an underground reservoir, it is necessary to drill a well into the reservoir, to a desired depth relative to the surface, to case it to protect the wellbore, to cement the casing so that the casing is fixedly attached to the well, and then to perforate the casing to connect the wellbore/casing to the subterranean formation to extract the oil and/or gas. This process of connecting the wellbore to the subterranean formation may include a step of plugging a previously fractured stage of the well with a plug, a step of perforating a portion of the casing, corresponding to a new stage, with a perforating gun string such that various channels are formed to connect the subterranean formation to the inside of the casing, a step of removing the perforating gun string, and a step of fracturing the various channels of the new stage. These steps are repeated until all the stages of the formation are fractured.

During the perforating step for a given stage, perforating guns of the perforating gun string are used to create perforation clusters in the casing of the well. Clusters are typically spaced along the length of a stage (a portion of the casing that is separated with plugs from the other portions of the casing), and each cluster comprises multiple perforations (or holes). Each cluster is intended to function as a point of contact between the wellbore and the formation. Each perforation in the casing is achieved by using a shaped charge. The shape charges are carried within the perforating guns. After being fired, each shaped charge makes not only a hole in the casing of the well, but also a corresponding tunnel in the formation around the well. The size of the hole in the casing and consequently the size of the tunnel in the formation depends on the type and size of the shaped charge.

As there are many shaped charges types and sizes on the market, and the conditions in the wells vary from location to location due to the subsurface material, pressure, temperature, oil and water content, etc., there is a need to evaluate and test the impact a given shaped charge has on a given casing and a given formation's structure. Various testing devices exist and are configured to receive one or more shaped charges and a formation sample and to simulate the conditions in the well when a shape charge is detonated. Thus, the hole's size in the casing and the length of the perforating tunnel in the sample material may be studied and measured at the subsurface, which helps in designing shaped charges for the various jobs in the field.

An example of such testing device 100 is shown in FIG. 1 and it includes a pressurized enclosure 102 that is configured to resist to a high internal pressure Pe, e.g., 10,000 psi. The internal pressure Pe is controlled through an external pipe 104, which is connected to an external accumulator 106. The pressure Pe is adjusted to reproduce the overburden pressure that is typically exerted by the subsurface material at a given depth. A sample material 110 is covered with a jacket 112 and placed inside the enclosure 102 for testing. The sample material 110 may be selected from a quarry to have a chemical composition and structure as close as possible to the material around the well. The jacket 112 maintains the sample material confined.

A perforating gun 120 having a shaped charge 122 is placed into a chamber 114 defined by a well head 108, which is attached to the enclosure 102. The chamber 114 simulates the interior of the wellbore. For this reason, a wellbore accumulator 116 is connected, via an external pipe 118, to the chamber 114 and the pressure supplied by the accumulator 116 simulates the pressure Pw inside the wellbore. A steel plate 124 and a concrete slab 128 are placed between the perforating gun 120 and the sample material 110, to simulate the casing that lines the wellbore and the concrete that fixes the casing in the wellbore. Another steel plate 130 is placed at the other end of the sample material 110 to hold the sample material fixed inside the enclosure 102. A pore pressure Pp is provided by a pore pressure accumulator 132, through an external pipe 134, to the steel plate 130 to simulate the formation pressure acting on the sample material 110. An external pipe is defined herein as a pipe that extends between two elements so that at least a portion of the pipe is in neither element.

In this way, the three accumulators 106, 116, and 132 simulate the corresponding overburden pressure, wellbore pressure and formation pressure that exist in the well, at the location where the shape charge is detonated. The relationships between these three pressures have a strong impact on the hole made by the shape charge 122 onto the simulated casing 124, and also onto the simulated perforating tunnel 140 that would likely be made in the formation material (the sample material 110 in the testing). By applying the correct pressures to the testing system 100, it is expected to obtain accurate sizes for the perforations made in the casing and the perforating tunnels made in the formation in actual perforating cases.

However, the inventors have noted that the pressures delivered by the accumulators 106, 116, and 132 when the shaped charge 122 is fired do not match exactly the desired pressures set up by the operator of the testing system and also these pressures are typically made available too late, i.e., after the shaped charge has been fired. All these imperfections may severely alter the accuracy of the results obtained with the testing system 100, which is undesired.

For these reasons, there is a need of a new testing system that overcomes these problems and provide accurate and instantaneous pressures at the time the shaped charge is fired.

SUMMARY

According to an embodiment, there is a testing system for a shaped charge of a perforating gun. The testing system includes a housing, a casing assembly located inside the housing, a perforating gun having at least one shaped charge, the perforating gun being located within the casing assembly, a sample material located within the housing, and in direct contact with the casing assembly, a wellbore accumulator in direct contact with the casing assembly and configured to supply a first fluid, at a wellbore pressure, inside the casing assembly, and a formation accumulator in direct contact with the sample material and configured to supply a second fluid, at a formation pressure, on the sample material.

According to another, there is a method for testing an impact of a shaped charge on a metal plate. The method includes placing a perforating gun within a casing assembly, wherein the perforating gun has at least one shaped charge, attaching a sample material to the casing assembly, placing the casing assembly and the sample material within a housing, connecting a wellbore accumulator in direct contact with the casing assembly to supply a first fluid, at a wellbore pressure, inside the casing assembly, and connecting a formation accumulator in direct contact with the sample material to supply a second fluid, at a formation pressure, on the sample material.

According to yet another embodiment, there is a testing system for testing an impact of a shaped charge on a metal plate. The testing system includes a housing, a perforating gun located within the housing and having a shaped charge, a curved metal plate located adjacent to the perforating gun and facing the shaped charge, and a jet arrester block located within the housing and holding the curved metal plate.

BRIEF DESCRIPTION OF THE DRAWINGS

The accompanying drawings, which are incorporated in and constitute a part of the specification, illustrate one or more embodiments and, together with the description, explain these embodiments. In the drawings.

DETAILED DESCRIPTION

The following description of the embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to a perforating gun having a single shaped charge. However, the embodiments discussed herein may be used for perforating guns having plural shaped charges.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

According to an embodiment, a novel testing system includes a first accumulator directly connected to a head of a wellbore and a second accumulator directly connected to a sample material. In one application, there are no pipes between the accumulators and the wellbore and the sample material. By removing the pipes that traditionally connect the accumulators to the various parts of the testing system, the inventors have noted that the pressure delivered by the accumulators is more accurately and more quickly delivered to the desired elements of the testing system. This is so because the pipes in the traditional testing systems act a brake that slows down the movement of the pressurized fluid while when the pipe is removed, this delay is also removed.

According to another embodiment, which is discussed later, a testing system may be implemented to more accurately determine the size and shape made by the shaped charge into a curved piece of casing. This system uses a pressurized enclosure to host the perforating gun with one or more shaped charges and also to hold a curved part of the casing next to the shaped charge. A fluid gap between the shaped charge and the curved part can be adjusted as desired and the pressure of the fluid in the gap and the chemical structure of the fluid in the gap may be controlled to simulate actual wellbore conditions. The shaped charge is then fired into the curved part of the casing under these controlled conditions. The perforated curved part of the casing is then removed from the testing device and the perforation made by the shaped charge is then inspected and measured for ascertaining the capabilities of the shaped charge. These embodiments are now discussed in more detail based on the drawings.

Figure 1:
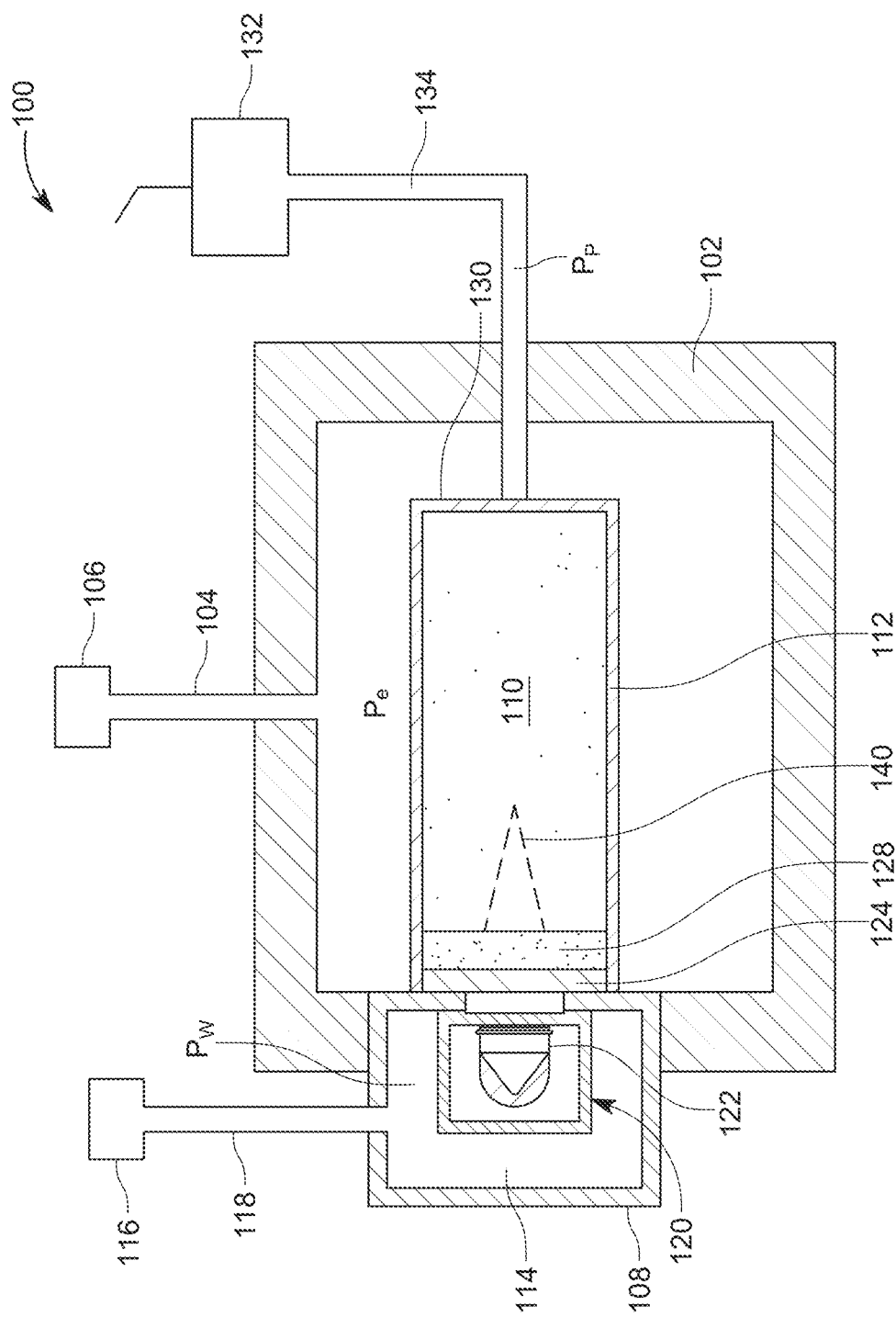
FIG. 1 illustrates a testing system for determining the effect a shaped charge of a perforating gun has on a casing.
Figure 2:
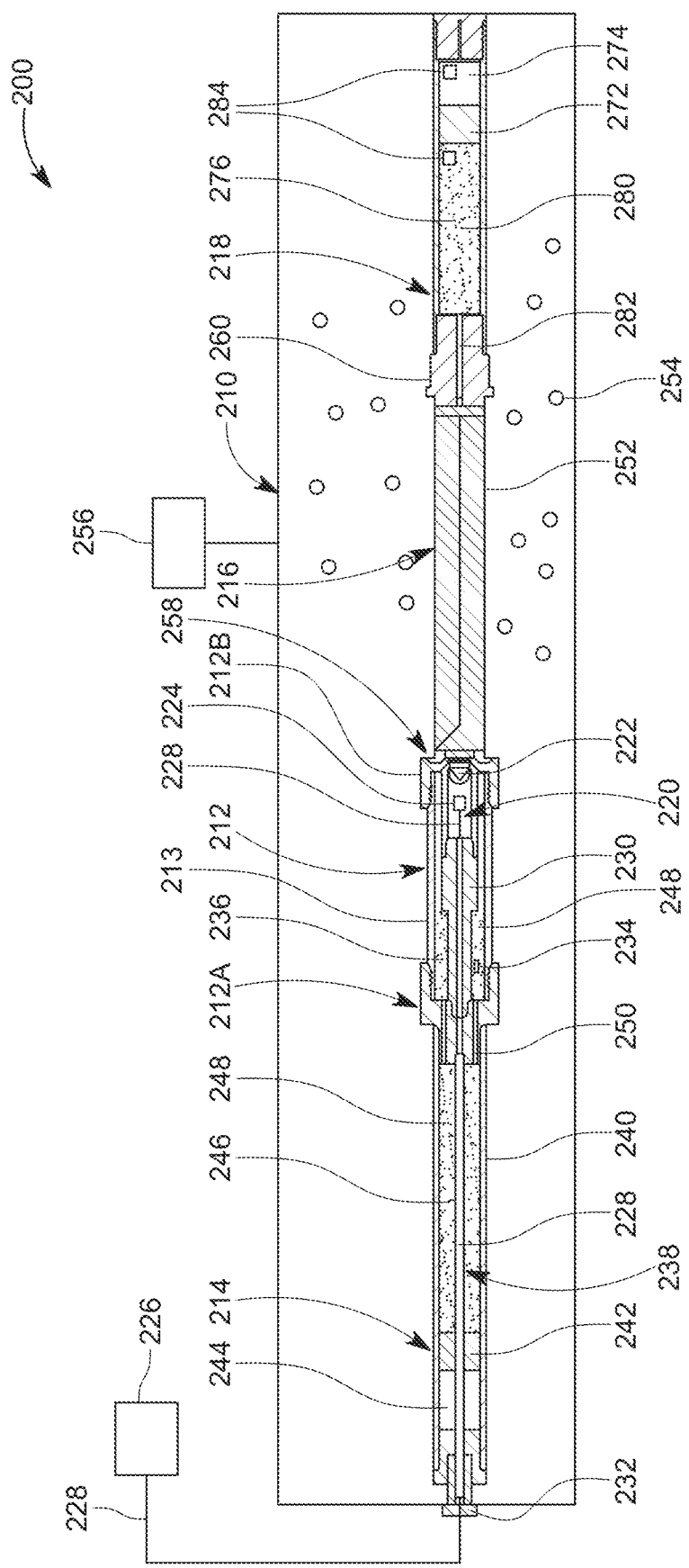
FIG. 2 illustrates a novel testing system that has a wellbore accumulator and a formation accumulator connected with no pipes to a casing assembly and a sample formation, respectively.

FIG. 2 shows a novel testing system 200 that has a pressurized housing 210 configured to hold not only the perforating gun and the casing assembly, but also the wellbore and formation accumulators so that the casing assembly is directly connected to the wellbore accumulator and the sample formation is directly connected to the formation accumulator. In this way, there are no pipes connecting the accumulators to the elements of the testing system, differently from the testing system shown in FIG. 1. More specifically, FIG. 2 shows a casing assembly 212 being directly connected to the wellbore accumulator 214 and the sample formation 216 is directly connected to the formation accumulator 218. The casing assembly 212 is in direct contact with the sample formation 216. In one embodiment, the wellbore and formation accumulators are gas over liquid piston style accumulators, i.e., an accumulator that has two chambers, one filled with a compressed gas and one filled with a fluid and the two chambers are separated by a moving piston. When necessary to discharge the fluid into a hydraulic setting, the piston is let free and the high-pressured gas pushes the piston toward the fluid filled chamber, thus quickly discharging the fluid into the hydraulic circuit. Each accumulator may hold a different liquid, consistent with the underground conditions. The housing 210 is configured to withstand a high pressure, i.e., about 20,000 psi.

FIG. 2 shows the casing assembly 212 having a casing 213, which is being treaded into first and second heads (also called top and bottom heads) 212A and 212B, respectively. The casing 213 may be selected to have the size and thickness as the casing that is actually provided in the well. Inside the bore of the casing 213, a perforating gun 220 is placed. The perforating gun 220 has a shaped charge 222 that is located to face the sample material 216, as in an actual well. A detonator 224 may also be placed in the perforating gun, for initiating the shaped charge 222. The detonator may include a detonation cable. The detonator is controlled by an external controller 226, through an electrical cable 228. The controller 226 may be a processor, a laptop, or any computing device having a processor, a memory and an input/output interface that is capable of communicating with the detonator and with various instrumentation/sensor places in the housing 210.

The perforating gun 220 is connected to a gun holder 230 that holds the gun inside the bore of the casing 213. The position of the gun holder 230 inside the casing 213 may be adjusted to obtain the desire gap between the perforating gun 220 and the bottom head 2128. The electrical cable 228 extends through the gun holder 230 and also through the wellbore accumulator 214 and then exits the housing 210, through a corresponding port 232, to arrive at the controller 226, which is placed outside the housing 210. One or more sensors 234 are placed in the annulus 236, formed between the gun holder 203 and/or the perforating gun 220, and the casing 213. The one or more sensors 234 are connected to the electrical cable 228 and supply information to the controller 226. The one or more sensors may include a pressure sensor for monitoring the pressure and its changes before the blast of the shaped charge, during the blast, and after the blast. The readings from this sensor are expected to describe the pressure inside the well.

The electrical cable 228 extends through an inner tube (made of metal, for example) 238 of the wellbore accumulator 214, from the top head 212A of the casing assembly 212, to the port 232. The inner tube 238 extends all the way through the body 240 of the wellbore accumulator 214. FIG. 2 shows a piston 242 located inside the body 240 of the wellbore accumulator 214, separating a gas chamber 244 from a fluid chamber 246. The gas chamber 244 stores the compressed gas while the fluid chamber 246 stores a first fluid 248, which simulates the wellbore fluid. The first fluid 248 is free to enter the annulus 236 in the casing assembly 212, through one or more channels 250. The one or more channels 250 are formed in the well head 212A that fluidly communicate the fluid chamber 246 with the annulus 236 of the casing. These channels 250 are very short, in the order of cm, and their number may be selected so that no or minimal resistance is present between the wellbore accumulator 214 and the casing assembly 212.

The sample material 216 is encased by a sleeve or jacket 252, which can be made of plastic or rubber or any composite material. To simulate the overburden pressure that is experienced by the actual formation material around the well at a given depth, a fluid 254 is present inside the housing 210, around the sample material 216, and a pressure of the fluid 254 may be controlled with a compressor or accumulator 256. Thus, the pressure of the fluid 254 simulates the pressure of the overburden. The sample material 216 is sandwiched between a metal-concrete assembly 258 and a metal head 260, which may be the end of the formation accumulator 218.

Figure 3:
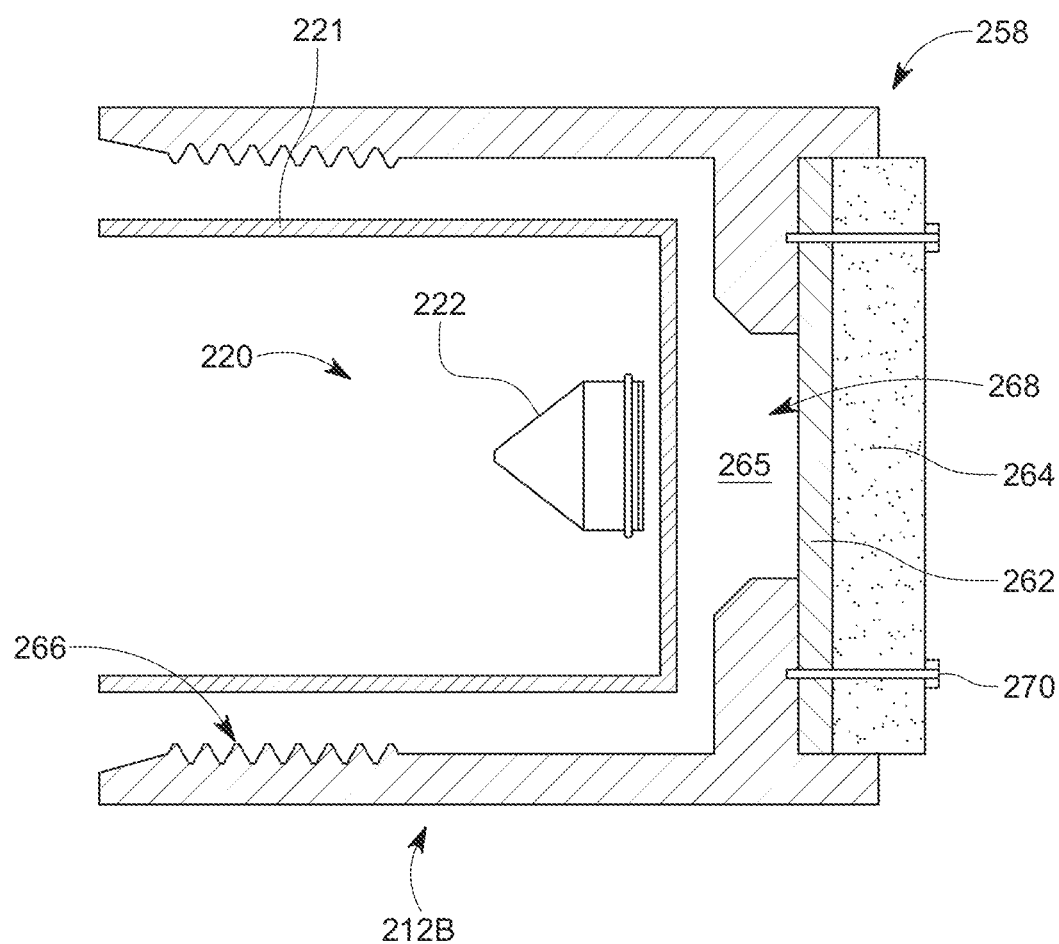
FIG. 3 illustrates a top head of a casing assembly used with the novel testing system.

The metal-concrete assembly 258 includes a metal plate 262 and a concrete portion 264 that are formed in direct contact, as shown in FIG. 3. This figure shows the bottom head 212B, which has a circular structure, with the threads 266 that engage the casing 213 (not shown). Both ends of the bottom head 212B are open. One of these openings is configured to receive the metal plate 262, which simulates the actual casing of the well, and to also receive the concrete portion 264, which simulates the concrete around the casing in the well. The metal plate 262 and the concrete portion 264 are attached to the bottom head 2128 with screws 270. Other means may be used to attach the metal plate 262 and the concrete portion 264 to the bottom head 2128. As the metal plate 262 simulates the casing and the concrete portion 264 simulates the concrete in the well, these two components of the testing system may be replaced to have different thicknesses and/or compositions, to simulate any actual well.

After the shape charge is shot, the metal plate, concrete portion, and the sample material can be removed from the testing system and the holes/perforations/channels made into them can be measured to determine the effect of the shaped charge on them. Various other tests may be made on these elements to learn more about their behavior under well conditions. Note that the shaped charge 222, which is also illustrated in FIG. 3, is provided behind the tube carrier 221 of the perforating gun 220, and a fluid gap 265 is present between the tube carrier 221 and the metal plate 262, exactly as is the case in an actual well. The gun holder 230, shown in FIG. 2, may be moved along a longitudinal direction of the gun 220, to adjust the fluid gap 265 as necessary. During testing, the first fluid 248 is present in the fluid gap 265, simulating the fluid well in the actual well. All these elements and parameters may be adjusted to simulate as closely as possible the actual perforating gun inside the well.

Returning to FIG. 2, the formation accumulator 218 also has a piston 272 that separates a compressed gas chamber 274 from a fluid chamber 278. The compressed gas chamber 274 holds a pressured gas while the fluid chamber 278 holds a second fluid 280, which is discharged through one or more channels 282 into the sample material 216. The one or more channels 282 is formed into the metal head 260. The fluid 280 may be an oil-based fluid that simulates the oil and gas reservoir around the actual well. When activated, the compressed gas pushes the piston 272 so that the second fluid 280 is discharged from the fluid chamber 278 into the sample material 216, to simulate the pore or formation pressure in the actual oil and gas reservoir. The activation of all the accumulators and/or compressors discussed herein may be coordinated by the controller 226 as each accumulator may have a corresponding valve that prevents the corresponding fluid from leaving the fluid chamber. When the valve is opened, the high pressure of the compressed gas pushes the corresponding piston and expels the fluid outside the accumulator. One or more sensors 284 may be placed in the formation accumulator 218 to measure the gas pressure and also the pressure on the sample material, i.e., the formation pressure. All the sensors are connected in a wired or wireless manner to the controller 226.

Figure 4:
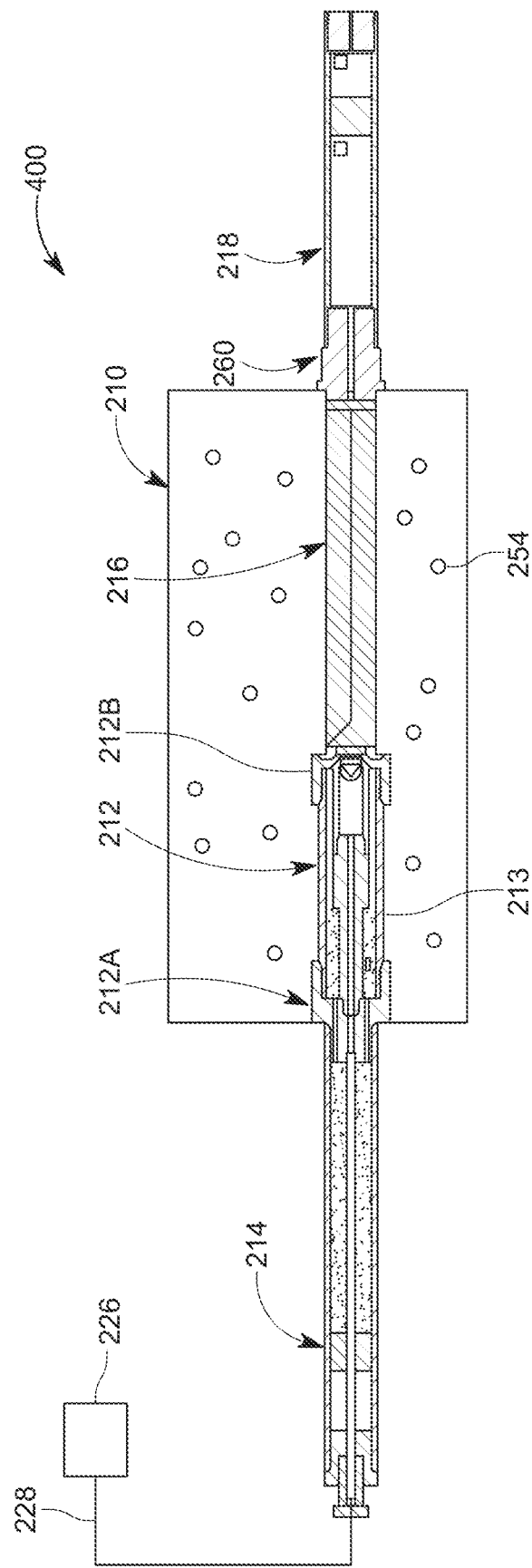
FIG. 4 illustrates another novel testing system that has a wellbore accumulator and a formation accumulator connected with no pipes to a casing assembly and a sample formation, respectively.

In an alternative embodiment, as illustrated in FIG. 4, the testing system 400 has the accumulators 214 and 218 situated outside the housing 210, but still in direct contact with the top head 212A and the sample material 216, so that no external piping is necessary to link the accumulators to the top head and the sample material. For both the embodiments shown in FIGS. 2 and 4, the housing 210 can be opened so that access to the sample material and the perforating gun is possible. Also, the top and bottom heads of the casing can be opened/removed to further provide access to the perforating gun. The compressed gas chambers of the accumulators 214 and 218 may be connected to corresponding compressors (not shown) or to a same compressor (not shown) to compress the gas to the desired pressure and to recharge them when necessary. The external controller 226 is configured to coordinate these compressors to obtain the desire pressure of the compressed gas. In one application, plural accumulators may be mounted to the top and bottom heads. While the present embodiments have used gas over fluid accumulators as they deliver a higher pressure than other accumulators, other type of accumulators may be used.

Figure 5:
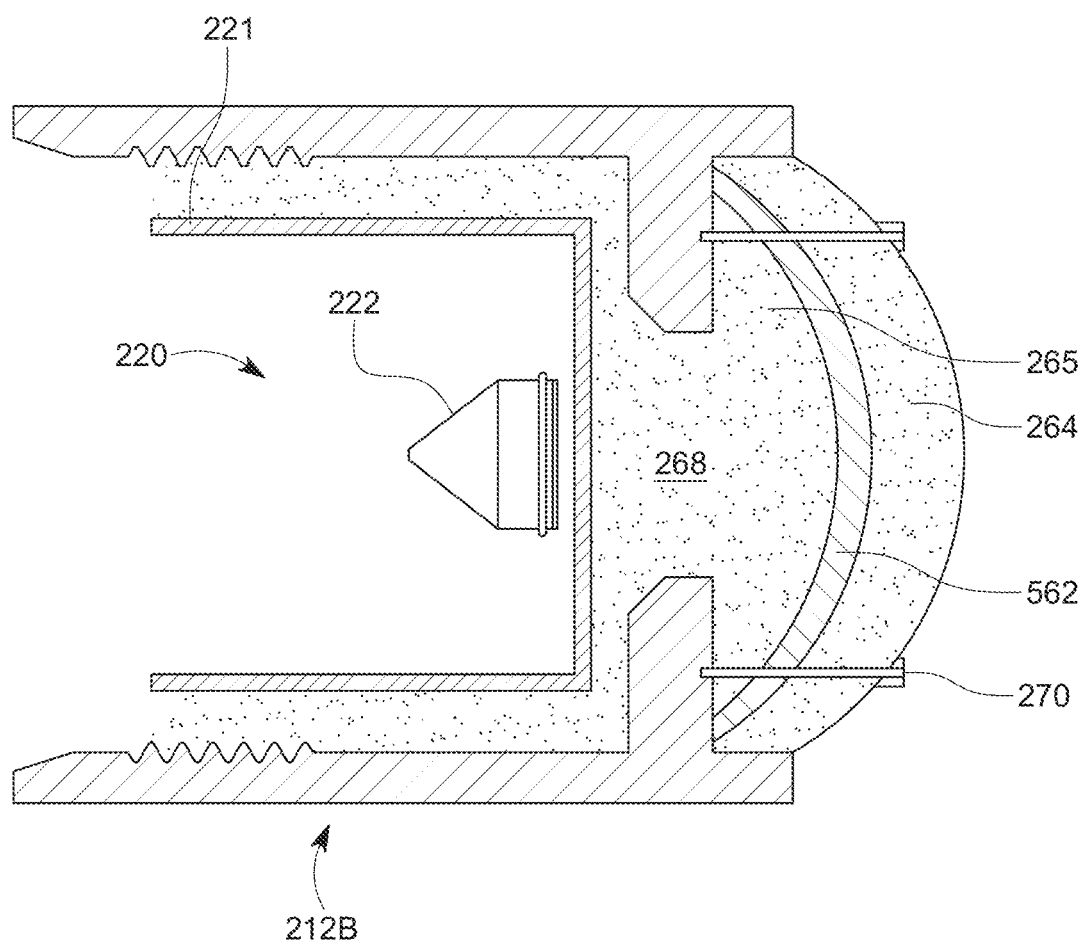
FIG. 5 illustrates a top head of the casing assembly receiving a curved metal plate for testing.

The testing systems 200 and 400 test the impact of the shaped charge on the metal plate 262 under various conditions that can be adjusted, e.g., wellbore pressure, overburden pressure, formation pressure, fluid gap between the gun and the casing, the composition of the fluid gap, the composition of the fluid released into the sample material, the composition of the fluid creating the overburden pressure, the temperature of these fluids, the thickness and consistency of the cement between the casing and the formation, and the actual chemical composition of the formation. However, the traditional systems and the systems presented in the figures herein use a flat metal plate 262. The actual casing in the well is not flat, but rather has a circular cross-section. Thus, to further improve the accuracy of the testing results, the testing systems 200 and 400 may be modified to accept a curved metal plate 562, as illustrated in FIG. 5. The curvature of the curved metal plate 562 may be selected to have any desired value, to mimic the actual casing in the well. The curved metal plate 562, similar to the flat metal plate 262, is attached to a concrete portion 264 and then removably attached, for example, with bolts or screws, to the bottom head 2128 of the casing assembly 213.

Figure 6:
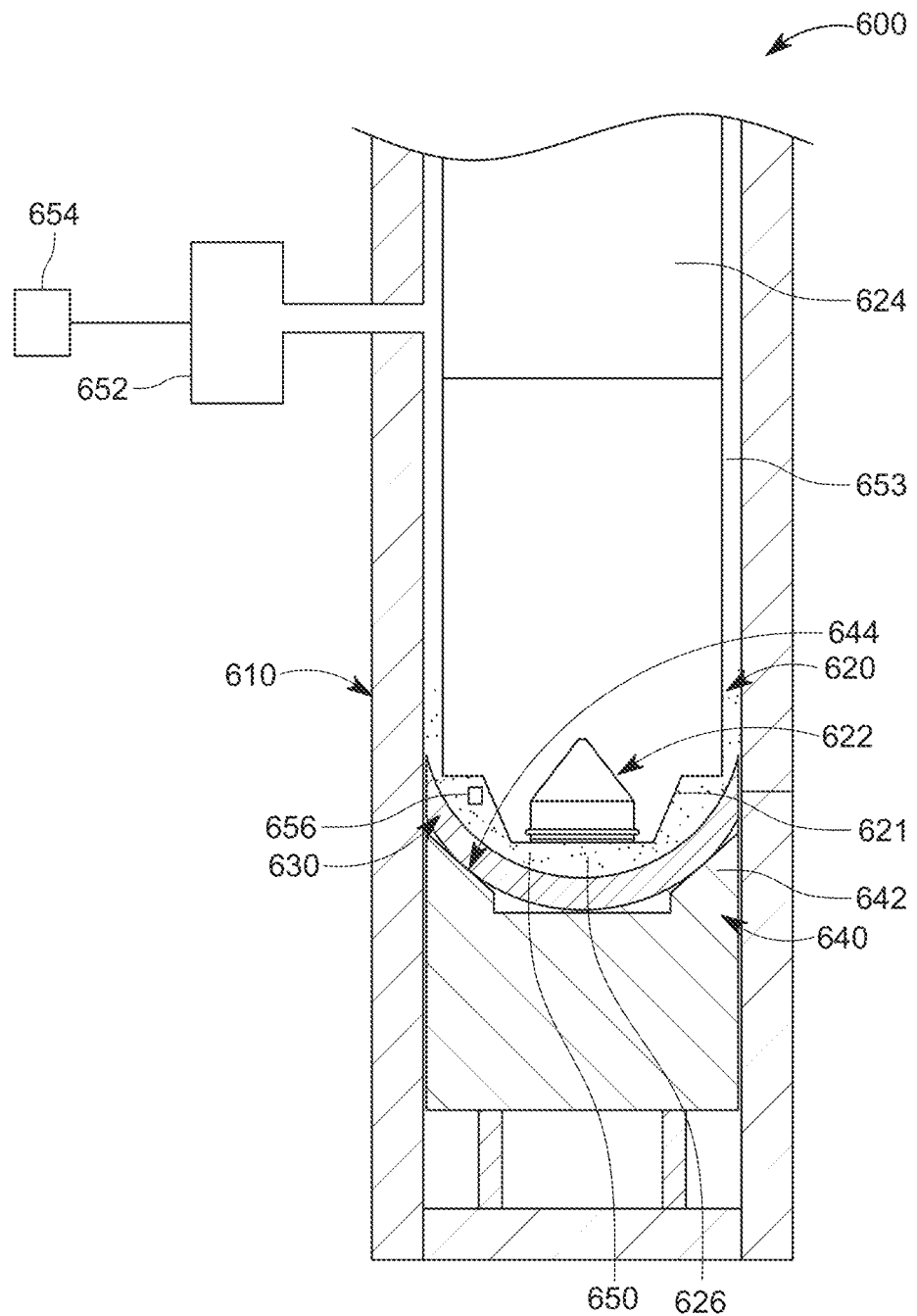
FIG. 6 illustrates another novel testing system that uses only curved metal plates.

In another embodiment, as illustrated in FIG. 6, a testing system 600 may be configured to study the impact of firing a shaped charge into a curved metal plate with no sample material. To achieve this testing system, either one of the testing systems 200 or 400 may be modified accordingly, or the testing system 600 may be a standalone system that complements a lab having the testing system 200 or 400. For ease of description, it is assumed herein that the testing system 600 is a standalone system. The system includes a pressure housing 610 that is configured to resist to a high pressure, for example, up to 20,000 psi. The pressure inside the housing 610 is intended to simulate the pressure inside an actual well. The housing 610 has an opening (not shown) through which a perforating gun 620 is lowered toward the curved metal plate 630, which simulates the casing. The curved metal plate 630 is supported by a jet arrester device 640, which is also placed inside the housing 610. The jet arrester device 640 may be made of a metal and this part is designed to absorb and stop the jet generated by the shaped charge 622. The jet arrester device is shaped to have a circular shoulder 642 that has an inclined top plane 644, for supporting the curved profile of the curved metal plate 630. Thus, the jet arrester device 640 is configured to hold the curved metal plate 630. Because of the vertical arrangement illustrated in FIG. 6, the curved metal plate 630 simply sits on the jet arrester device 640, with no need of using any attaching means.

The perforating gun 620 may be attached to a holder 624, that is configured to move up and down relative to the housing 610, to adjust the gap 626 between the curved metal plate 630 and the housing 621 of the perforating gun 620. The gap 626 may be filled with a wellbore fluid 650 to simulate the well conditions. A pressure of the wellbore fluid 650 may be controlled with a compressor 652, which is fluidly connected to the annulus 653 formed by the inner surface of the housing 610 and the outer surface of the perforating gun 620. A controller 645, outside the housing 610, may be connected to the compressor to control the pressure inside the annulus 653. One or more sensors 656 may be placed in the gap 626 or the annulus 653 to measure the pressure and/or the temperature. The sensor is also connected to the controller 654.

After the shaped charge 622 is fired, the housing 610 may be opened, the perforating gun may be removed, after which the curved metal plate 630 is removed for analysis and measurements. Then, a new plate may be provided over the jet arrester 640 and a new shaped charge may be tested. Thus, for the testing system 600, there are a couple of parameters that can be changed for determining the desired perforation into the curved metal plate 630. These parameters include one or more of: the sized of gap between the perforating gun and the curved metal plate, the type and size of the shaped charge, the liner of the shaped charge, the angle of the shaped charge, the type of explosive material used in the shaped charge, the pressure in the gap, the thickness of the curved metal plate, the radius of curvature of the curved metal plate, the material of the curved metal plate, etc.

Figure 7:
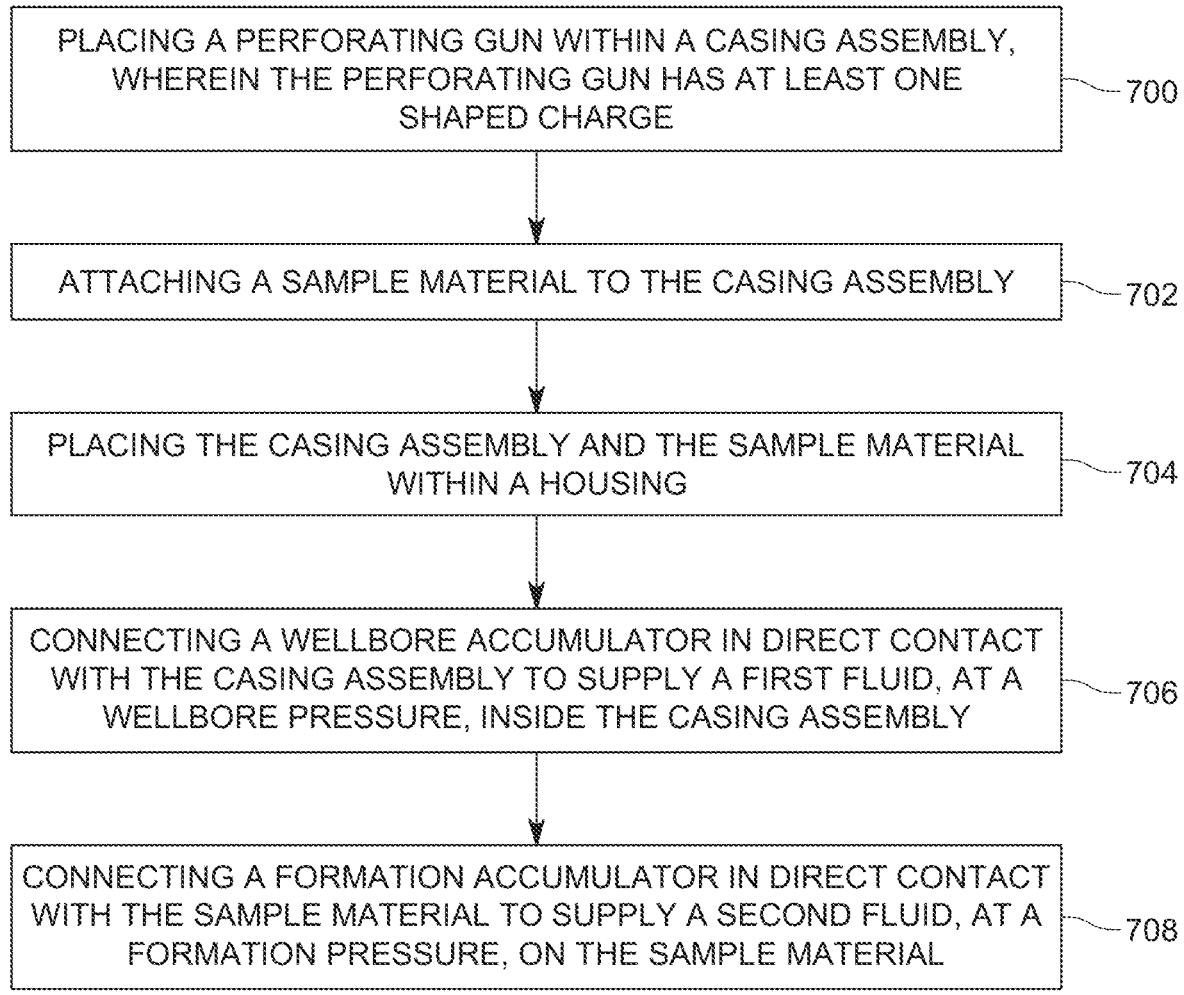
FIG. 7 is a flowchart of a method for testing a metal plate with the novel testing system that has a wellbore accumulator and a formation accumulator connected with no pipes to a casing assembly and a sample formation, respectively

A method for testing an impact of a shaped charge on a metal plate when using the testing system 200 or 400 is now discussed with regard to FIG. 7. The method includes a step 700 of placing a perforating gun within a casing assembly, wherein the perforating gun has at least one shaped charge, a step 702 of attaching a sample material to the casing assembly, a step 704 of placing the casing assembly and the sample material within a housing, a step 706 of connecting a wellbore accumulator in direct contact with the casing assembly to supply a first fluid, at a wellbore pressure, inside the casing assembly, and a step 708 of connecting a formation accumulator in direct contact with the sample material to supply a second fluid, at a formation pressure, on the sample material.

In one application, the method may further include a step of pressurizing the housing to an overburden pressure, a step of firing the shaped charge to make a perforation into a metal plate that is attached to the casing assembly, and a step of releasing the first and second fluids from the wellbore and formation accumulators to simulate actual pressures within a well. The method may further include removing the metal plate from the housing, and measuring a size of the perforation made into the metal plate. There are no pipes between the wellbore accumulator and the casing assembly, and there are no pipes between the formation accumulator and the sample material. In one application, each of the wellbore accumulator and the formation accumulator are located within the housing. The casing assembly may include a casing tube, a top head configured to be attached with threads to the casing tube, and a bottom head configured to be attached with threads to the casing tube. The top head has one or more passages that communicate an inside of the wellbore accumulator with an inside of the casing tube, and the bottom head has an opening covered by the metal plate and a concrete portion attached to the metal plate. The method may further include placing a pressure sensor within the casing assembly, and connecting an electrical cable, which extends from the perforating gun, through the casing assembly and through a center pipe of the wellbore accumulator, to an external controller. The method may also include controlling a composition of the sampling material, a size of the shaped charge, a type of the shaped charge, a fluid composition within the casing assembly, a pressure of the fluid composition, an overburden pressure acting on the sampling material, a formation pressure action on an end of the sampling material, a thickness of a metal plate that is located between the shaped charge and the sample material, and a thickness of a concrete layer that is located between the metal plate and the sample material.

It is noted that the controller or other means may be used to control the release time of the well fluid in the casing assembly, the fluid injected into the sample formation, and the pressure of the fluid that simulates the overburden pressure. These time releases may be coordinated in one embodiment to coincide with the firing of the shaped charge. The overburden pressure may be maintained constant during the entire testing process The testing system 600 may be used to analyze the impact a shaped charge is making on a curved metal plate when detonated. For this investigation, the user will select a curved metal plate that best describes the casing of an actual well. The radius of curvature, the thickness of the plate and the composition of the plate may be selected accordingly. Then the selected curved metal plate is placed within the housing of the testing system, directly on top of the jet arrester device, with no concrete material present. The perforating gun having the shaped charge is then lowered into the housing of the testing system, just above the curved metal plate. A gap distance between the housing of the perforating gun and the curved metal plate is selected to simulate an actual perforating operation in a well. A fluid is provided into the annulus and the gap formed by the perforating gun and the curved metal plate to simulate the well fluid. The housing of the testing system is then sealed and a pressure of the fluid is increased to simulate the actual pressure inside the well. At this time, an external controller fires the shaped charge to perforate the curved metal plate. After the pressure is released from the housing of the testing system, the curved metal plate is removed for analysis. Another curved metal plate may then be studied with a different shaped charge.

The disclosed embodiments provide testing systems for perforating guns and these systems are capable of simulating underground conditions with high accuracy and speed. It should be understood that this description is not intended to limit the invention. On the contrary, the exemplary embodiments are intended to cover alternatives, modifications and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. A testing system for testing an impact of a shaped charge on a metal plate, the testing system comprising:
   a housing;
   a perforating gun located within the housing and having a shaped charge;
   a concave metal plate located adjacent to the perforating gun and facing the shaped charge; and
   a jet arrester block located within the housing and holding the concave metal plate.

2. The testing system of claim 1, further comprising:
   a holder attached to the perforating gun and configured to move the perforating gun relative to the concave metal plate;
   a compressor fluidly connected to the housing and configured to control a pressure of a fluid present inside the housing;
   a sensor located inside the housing; and
   a controller located outside the housing and configured to receive a signal from the sensor.

3. The testing system of claim 2, wherein the perforating gun forms an annulus with the housing.

4. The testing system of claim 3, wherein the sensor is disposed within the annulus.

5. The testing system of claim 2, wherein a gap is disposed between the perforating gun and the concave metal plate.

6. The testing system of claim 5, wherein the sensor is disposed within the gap.

7. The testing system of claim 5, wherein the holder is configured to adjust a width of the gap.

8. The testing system of claim 2, wherein the sensor comprises a pressure sensor.

9. The testing system of claim 2, wherein the sensor comprises a temperature sensor.

\* \* \* \* \*